United States Patent [19]

Southwick

[11] Patent Number: 5,144,965
[45] Date of Patent: Sep. 8, 1992

[54] SMOKING COMPOSITIONS CONTAINING A VANILLIN-RELEASE ADDITIVE

[75] Inventor: Everett W. Southwick, Richmond, Va.

[73] Assignees: Philip Morris Incorporated, New York, N.Y.; Philip Morris Products Inc., Richmond, Va.

[21] Appl. No.: 700,401

[22] Filed: May 15, 1991

[51] Int. Cl.$^5$ .......................... A24B 3/12; A24D 1/02
[52] U.S. Cl. ..................................... 131/276; 131/365
[58] Field of Search ................................ 131/276, 365

[56] References Cited

U.S. PATENT DOCUMENTS 3,499,452 3/1970 Kallianos et al. .
4,092,988 6/1978 Van Auken et al. .
4,236,532 12/1980 Schweizer et al. .
4,612,942 9/1986 Dobberstein et al. .
4,643,205 2/1987 Redding et al. .

Primary Examiner—V. Millin
Attorney, Agent, or Firm—James E. Schardt

[57] ABSTRACT

This invention provides smoking compositions which contain a vanillin carboxylate type flavorant-release additive.

Under cigarette smoking conditions, a combustible filler and/or paper wrapper additive such as 5-carboxyethylvanillin pyrolyzes and releases ethylvanillin as a volatile flavorant component of the cigarette smoke.

23 Claims, No Drawings

SMOKING COMPOSITIONS CONTAINING A VANILLIN-RELEASE ADDITIVE

CROSS-REFERENCE TO RELATED PATENT APPLICATION

The present patent application has subject matter related to the disclosure of copending patent application Ser. No. 565,126, filed Aug. 10, 1990.

BACKGROUND OF THE INVENTION

A variety of flavorants have been developed and proposed for incorporation into tobacco products. Illustrative of such tobacco flavorants are those described in U.S. Pat. Nos. 3,580,259; 3,625,224; 3,722,516; 3,750,674; 3,879,425; 3,881,025; 3,884,247; 3,890,981; 3,903,900; 3,914,451; 3,915,175; 3,920,027; 3,924,644; 3,937,228, 3,943,943; 3,586,387; 3,379,754; and the like.

J. C. Leffingwell et al "Tobacco Flavoring For Smoking Products" (R. J. Reynolds Publication, 1972) recites a listing of desirable flavorants for smoking compositions, which include phenols, terpenols and lactones such as guaiacol, 1-undecanol and 5-dodecalactone.

The high degree of volatility and ease of sublimation of flavorant additives in tobacco products have presented problems in the manufacturing operations, and have resulted in a decreased shelf-life of the products due to losses of flavorant by evaporation on storage.

Recent developments have involved incorporating a low volatility organic additive to a smoking composition, which under smoking conditions is pyrolyzed into one or more fragments that function to improve the taste and character of mainstream tobacco smoke, and in some cases a consequential improvement of sidestream smoke aroma.

U.S. Pat. No. 3,312,226 describes smoking tobacco compositions which contain an ester additive such as 1-menthyl linalool carbonate. Under smoking conditions pyrolysis of the carbonate ester releases menthol which flavors the mainstream smoke.

U.S. Pat. No. 3,332,428 and U.S Pat. No. 3,419,543 describe smoking tobacco compositions which contain a menthyl carbonate ester of a glycol or saccharide, which under smoking conditions decomposes to release free menthol into the mainstream smoke. U.S. Pat. No. 3,499,452 discloses similar smoking tobacco compositions in which a carbonate ester additive releases flavorant volatiles other than menthol.

U.S. Pat. Nos. 4,119,106; 4,171,702; 4,117,339; and 4,212,310 describe other oligomeric and polymeric carbonate ester derivatives which as constituents of smoking compositions are stable and non-volatile under storage conditions, and are adapted to release pyrolysis products under smoking conditions that improve the taste and aroma of the smoke.

U.S. Pat. Nos. 4,036,237; 4,141,906; and 4,178,458 describe β-hydroxyesters which as additives in smoking compositions pyrolyze into volatile aldehyde and ester flavorants under smoking conditions.

Of specific interest with respect to the present invention is the proposed utilization of an organic additive to a cigarette paper wrapper to enhance sidestream smoke aroma under smoking conditions. U.S. Pat. No. 4,804,002 describes a tobacco product wrapper containing a flavorant additive comprising a glycoside of a carbohydrate and phenolic compound. Under cigarette smoking conditions a flavorant additive such as ethyl-vanillyl-D-glucoside yields ethylvanillin and levoglucosan as pyrolysis products.

There is continuing research effort to develop low delivery smoking compositions which generate mainstream smoke with enhanced taste and sidestream smoke with a pleasant aroma under smoking conditions.

Accordingly, it is an object of this invention to provide smoking compositions having incorporated therein a flavorant-release component which is characterized by lack of mobility and/or volatility at ambient temperature.

It is another object of this invention to provide cigarette smoking products having a paper wrapper which has incorporated therein a flavorant-release additive which under normal smoking conditions imparts improved aroma to sidestream smoke.

It is a further object of this invention to provide carboxylate derivatives which are adapted to be incorporated into cigarette filler and/or paper wrapper components, and which under normal smoking conditions release vanillin or ethylvanillin as a volatile flavorant compound of the cigarette smoke.

Other objects and advantages of the present invention shall become apparent from the following description and example.

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.0001–5 weight percent, based on the total weight of filler, of a flavorant-release additive corresponding to the formula:

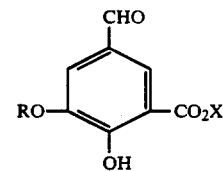

where R is methyl or ethyl, and X is hydrogen or an alkali or alkaline earth metal.

In another embodiment this invention provides a cigarette smoking product comprising (1) a combustible filler selected from natural tobacco, reconstituted tobacco and tobacco substitutes, and (2) a paper wrapper which has incorporated therein a flavorant-release additive corresponding to the formula:

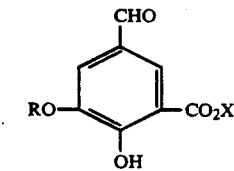

where R is methyl or ethyl, and X is hydrogen or an alkali or alkaline earth metal.

A cigarette smoking product in accordance with the present invention typically contains between about 0.01–5 weight percent of flavorant-release additive in the paper wrapper. The additive can be present as a surface coating or absorbed component of the paper wrapper, and/or the additive can be incorporated as a component of the adhesive formulation which is utilized to seal the sideseam of cigarette paper wrappers.

In a further embodiment an invention cigarette product contains between about 0.01-5 weight percent of flavorant-release additive in the paper wrapper, and contains between about 0.0001-5 weight percent of flavorant-release additive in the combustible filler, based on the weight of filler.

A present invention flavorant-release additive which is incorporated in smoking compositions as described above is a low volatility compound which under normal smoking conditions pyrolyzes into volatile constituents, one of which is vanillin or ethylvanillin which enhances the flavor and aroma of low delivery cigarette smoke:

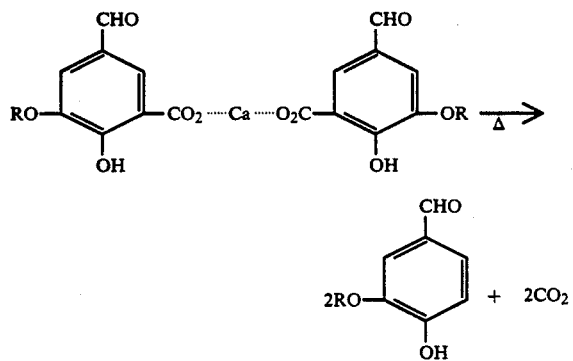

where R is methyl or ethyl.

A starting material such as 5-carboxyvanillin is a commercially available product (Apin Chemicals Ltd.). 5-Carboxyvanillin or 5-carboxyethylvanillin can be converted to an alkali or alkaline metal salt by reacting the carboxylic acid with an appropriate basic reagent in an inert solvent medium such as aqueous tetrahydrofuran.

The salt-forming reagent preferably is selected from basic compounds of alkali and alkaline earth metals such as sodium, potassium, lithium, magnesium, calcium, strontium and barium.

PREPARATION OF TOBACCO COMPOSITIONS

In a further embodiment the present invention provides a method of preparing a smoking composition which is adapted to impart flavor and aroma to mainstream and sidestream smoke under smoking conditions, which method comprises incorporating into natural tobacco, reconstituted tobacco or tobacco substitute between about 0.0001-5 weight percent, based on composition weight, of a flavorant-release additive corresponding to the formula:

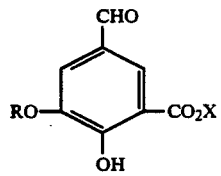

where R is methyl or ethyl, and X is hydrogen or an alkali or alkaline earth metal.

The invention flavorant-release additive can be incorporated into the tobacco or tobacco substitute in accordance with methods known and used in the art. Preferably the flavorant-release additive is dissolved in a solvent such as alcohol or aqueous alcohol and then sprayed or injected into the tobacco and/or tobacco substitute matrix. Such method ensures an even distribution of the flavorant-release additive throughout the filler, and thereby facilitates the production of a more uniform smoking composition. Alternatively, the flavorant-release additive may be incorporated as part of a concentrated tobacco extract which is applied to a fibrous tobacco web as in the manufacture of reconstituted tobacco. Another suitable procedure is to incorporate the additive in tobacco or tobacco substitute filler in a concentration between about 0.5-5 weight percent, based on the weight of filler, and then subsequently to blend the treated filler with filler which does not contain additive.

The term "tobacco substitute" is meant to include non-tobacco smoking filler materials such as are disclosed in U.S. Pat. Nos. 3,703,177; 3,796,222; 4,019,521; 4,079,742; and references cited therein, incorporated herein by reference.

As previously described hereinabove, an invention flavorant-release additive also can be incorporated in the paper wrapper of cigarette products, for the purpose of enhancing the aroma of cigarette sidestream smoke under smoking conditions. The additive can be applied to the paper wrapper in the form of a solution, or a suspension of fine particles. Alternatively, the additive can be included as an ingredient during the cigarette paper making process.

A further method of incorporating a flavorant-release additive in a cigarette smoking composition is by including the additive as an ingredient in the paper wrapper sideseam adhesive formulation which is employed in cigarette fabrication.

The following Example is further illustrative of the present invention. The specific ingredients and processing parameters are presented as being typical, and various modifications can be derived in view of the foregoing disclosure within the scope of the invention.

EXAMPLE

This Example illustrates the release of vanillin or ethylvanillin when an invention flavorant-release compound is subjected to pyrolysis conditions.

5-Carboxyvanillin is pyrolyzed in helium at 300° C. with a quartz tube/furnace pyrolysis unit. The volatile pyrolyzate is condensed at −50° C. in a 3 inch section of a 30 meter DB-5 fused silica capillary column.

This section of column is rapidly heated to the oven temperature after pyrolyzing the sample. The oven temperature, initially at 0° C. for 4 minutes, is programmed at 7° C. per minute to 280° C. Three minutes after the onset of pyrolysis, spectra over a range of m/z 33 to 500 are obtained by scanning every second. The third peak compound below is an impurity in the starting material.

| Peak | Relative area (%) |
|---|---|
| 1. carbon dioxide | 04.5 |
| 2. vanillin | 92.0 |
| 3. 5-carboxy-3,4-dimethoxybenzaldehyde | 03.5 |

Similar results are observed when the starting material is 5-carboxyethylvanillin, sodium vanillin-5-carboxylate, sodium ethylvanillin-5-carboxylate, potassium vanillin-5-carboxylate, potassium ethylvanillin-5-carboxylate, magnesium vanillin-5-carboxylate, magnesium ethylvanillin-5-carboxylate, calcium vanillin-5-carboxylate or calcium ethylvanillin-5-carboxylate. The released flavorant is vanillin or ethylvanillin, respectively.

What is claimed is:

1. A smoking composition comprising an admixture of (1) combustible filler selected from natural tobacco, reconstituted tobacco and tobacco substitutes, and (2) between about 0.0001-5 weight percent, based on the total weight of filler, of a flavorant-release additive corresponding to the formula:

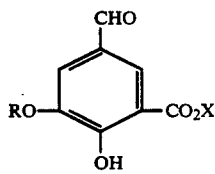

where R is methyl or ethyl, and X is hydrogen or an alkali or alkaline earth metal.

2. A smoking composition in accordance with claim 1 wherein the flavorant-release additive is 5-carboxyvanillin.

3. A smoking composition in accordance with claim 1 wherein the flavorant-release additive is 5-carboxyethylvanillin.

4. A smoking composition in accordance with claim 1 wherein the flavorant-release additive is sodium or potassium vanillin-5-carboxylate.

5. A smoking composition in accordance with claim 1 wherein the flavorant-release additive is sodium or potassium ethylvanillin-5-carboxylate.

6. A smoking composition in accordance with claim 1 wherein the flavorant-release additive is magnesium or calcium vanillin-5-carboxylate.

7. A smoking composition in accordance with claim 1 wherein the flavorant-release additive is magnesium or calcium ethylvanillin-5-carboxylate.

8. A cigarette smoking product comprising (1) a combustible filler selected from natural tobacco, reconstituted tobacco and tobacco substitutes, and (2) a paper wrapper which has incorporated therein a flavorant-release additive corresponding to the formula:

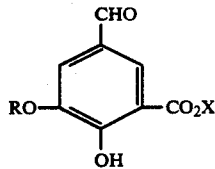

where R is methyl or ethyl, and X is hydrogen or an alkali or alkaline earth metal.

9. A cigarette smoking product in accordance with claim 8 wherein the paper wrapper contains between about 0.01-5 weight percent of flavorant-release additive.

10. A cigarette smoking product in accordance with claim 8 wherein the flavorant-release additive in the paper wrapper is 5-carboxyvanillin.

11. A cigarette smoking product in accordance with claim 8 wherein the flavorant-release additive in the paper wrapper is 5-carboxyethylvanillin.

12. A cigarette smoking product in accordance with claim 8 wherein the flavorant-release additive in the paper wrapper is sodium or potassium vanillin-5-carboxylate.

13. A cigarette smoking product in accordance with claim 8 wherein the flavorant-release additive in the paper wrapper is sodium or potassium ethylvanillin-5-carboxylate.

14. A cigarette smoking product in accordance with claim 8 wherein the flavorant-release additive in the paper wrapper is magnesium or calcium vanillin-5-carboxylate.

15. A cigarette smoking product in accordance with claim 8 wherein the flavorant-release additive in the paper wrapper is magnesium or calcium ethylvanillin-5-carboxylate.

16. A cigarette smoking product in accordance with claim 8 wherein the flavorant-release additive is a component of the sideseam adhesive of the paper wrapper.

17. A cigarette smoking product in accordance with claim 8 wherein the combustible filler contains between about 0.0001-5 weight percent, based on the weight of filler, of a flavorant-release additive corresponding to the formula:

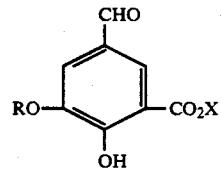

where R is methyl or ethyl, and X is hydrogen or an alkali or alkaline earth metal.

18. A cigarette smoking product in accordance with claim 17 wherein the flavorant-release additive in the combustible filler is 5-carboxyvanillin.

19. A cigarette smoking product in accordance with claim 17 wherein the flavorant-release additive in the combustible filler is 5-carboxyethylvanillin.

20. A cigarette smoking product in accordance with claim 17 wherein the flavorant-release additive in the combustible filler is sodium or potassium vanillin-5-carboxylate.

21. A cigarette smoking product in accordance with claim 17 wherein the flavorant-release additive in the combustible filler is sodium or potassium ethylvanillin-5-carboxylate.

22. A cigarette smoking product in accordance with claim 17 wherein the flavorant-release additive in the combustible filler is magnesium or calcium vanillin-5-carboxylate.

23. A cigarette smoking product in accordance with claim 17 wherein the flavorant-release additive in the combustible filler is magnesium or calcium ethylvanillin-5-carboxylate.

* * * * *